United States Patent [19]

Lutz et al.

[11] Patent Number: 4,927,449

[45] Date of Patent: May 22, 1990

[54] TRICYCLIC 1H-IMIDAZOLE-5-CARBOXYLIC ACID DERIVATIVES AS HERBICIDES

[75] Inventors: William R. Lutz, Riehen, Switzerland; Wim G. Verschueren, Antwerpen, Belgium; Hanspeter Fischer, Bottmingen, Switzerland; Guy R. E. Van Lommen, Berlaar, Belgium

[73] Assignee: Janssen Pharmaceutica N.V., Beerse, Belgium

[21] Appl. No.: 289,947

[22] Filed: Dec. 27, 1988

Related U.S. Application Data

[62] Division of Ser. No. 134,440, Dec. 17, 1987, abandoned.

[30] Foreign Application Priority Data

Dec. 23, 1986 [GB] United Kingdom ................. 8630759

[51] Int. Cl.$^5$ .................... A01N 43/02; A01N 43/48; C07D 403/00
[52] U.S. Cl. ........................................ 71/90; 548/336; 71/92
[58] Field of Search ....................... 548/336; 71/92, 90

[56] References Cited

U.S. PATENT DOCUMENTS 3,485,917 12/1969 Goedfroi et al. ...................... 71/78
3,873,297 3/1975 Kupelian ................................ 71/78
4,734,421 3/1988 Hammond et al. ................. 514/274

Primary Examiner—Mary C. Lee
Assistant Examiner—Robert C. Whittenbaugh
Attorney, Agent, or Firm—Charles J. Metz

[57] ABSTRACT

Novel herbicidal tricyclic 1H-imidazole-5-carboxylic acid derivatives, compositions containing these compounds as active ingredients, and a method for controlling weeds, preferably selectively in crops of useful plants.

17 Claims, No Drawings

TRICYCLIC 1H-IMIDAZOLE-5-CARBOXYLIC ACID DERIVATIVES AS HERBICIDES

This is a division of application Ser. No. 134,440, filed Dec. 17, 1987, now abandoned.

BACKGROUND OF THE INVENTION

A number of 1H-imidazole-5-carboxyilic acid derivatives are known from U.S. Pat. No. 3,485,917 as antifungal agents. Further, some of these compounds are described as active agents in a method for inhibiting bud growth in U.S. Pat. No. 3,873,297.

DESCRIPTION OF THE INVENTION

The present invention is concerned with herbicidally active tricyclic 1H-imidazole-5-carboxylic acid derivatives having the formula

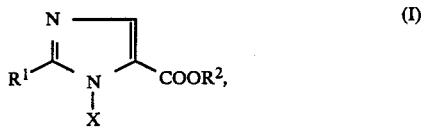

a stereochemically isomeric form thereof, or a salt thereof, wherein $R^1$ is hydrogen or mercapto, $R^2$ is hydrogen, $C_1$–$C_7$alkyl, $C_3$–$C_7$alkenyl, $C_3$–$C_7$alkynyl, $C_3$–$C_7$cycloalkyl, $C_1$–$C_7$alkyloxy-$C_1$–$C_7$alkyl or aryl$C_1$–$C_5$alkyl;

X is a radical of formula

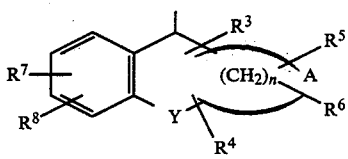

wherein

Y is O, $S(O)_m$, $NR^9$ or $CH_2$;

wherein m is zero, one or two;

$R^9$ is hydrogen, $C_1$–$C_5$alkyl, $C_1$–$C_5$alkanoyl or 4-methylphenylsulfonyl;

n is 1, 2 or 3;

A is a $C_1$–$C_5$alkanediyl or a $C_5$–$C_7$cycloalkanediyl radical;

$R^3$, $R^4$, $R^5$ and $R^6$ are each independently hydrogen, $C_1$–$C_5$alkyl, mono- and di(aryl)$C_1$–$C_5$alkyl, $C_1$–$C_5$alkyloxy, halo, $C_3$–$C_7$alkenyl, $C_1$–$C_5$alkyl substituted with one to three halo atoms, $C_1$–$C_5$alkyloxy substituted with one to three halo atoms, or aryl;

whereby the radicals $R^3$, $R^4$ and the bivalent radical A as defined above may be substituted on any carbon atom making up the Y-containing part of the tricyclic ring system, including any of the $CH_2$ moieties of the —$(CH_2)_n$— and Y fragments; provided that the bivalent radical A is not connected to the same carbon atom thus forming a spirocyclic ring system;

$R^7$ and $R^8$ are each independently hydrogen, $C_1$–$C_5$alkyl, $C_1$–$C_5$alkyloxy, halo, $C_1$–$C_5$alkyl substituted with one to three halo atoms, $C_1$–$C_5$alkyloxy substituted with one to three halo atoms, cyano, nitro, amino, mono- and di-$C_1$–$C_5$alkylamino or $C_1$–$C_6$alkylcarbonylamino; and aryl is phenyl optionally substituted with one to three substitutents each independently selected from $C_1$–$C_5$alkyl, $C_1$–$C_5$alkyloxy and halo.

Surprisingly, the compounds of formula (I) show strong herbicidal properties and are therefore useful to control weeds. These properties gain importance by the fact that some crops of useful plants are not damaged, or are only slightly harmed when treated with compounds of formula (I) at high dosages. Consequently, the compounds of formula (I) are valuable selective herbicides in crops of useful plants, such as sugar-beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1$–$C_5$alkyl denotes straight or branch chained saturated hydrocarbon radicals having from 1 to 5 carbon atoms, e.g. methyl, ethyl, propyl, 1-methylethyl, the four butyl isomers, the pentyl isomers; $C_1$–$C_7$alkyl includes $C_1$–$C_5$alkyl radicals and the higher homologs thereof having 6 or 7 carbon atoms; halo is fluoro, chloro, bromo or iodo, with fluoro and chloro being preferred; $C_3$–$C_7$- alkenyl defines straight and branched chained hydrocarbon radicals containing one double bond and having from 3 to 7 carbon atoms such as, for example, 2-propenyl, 3-butenyl, 2-butenyl, 2-pentenyl, 3-pentenyl, 2-methyl-2-propenyl, or 3-methyl-2-butenyl, with 2-propenyl and 2-methyl-2-propenyl being preferred; $C_3$–$C_7$alkynyl defines straight and branched chained hydrocarbon radicals containing one triple bond and having from 3 to 7 carbon atoms such as, for example, 2-propynyl, 2-butynyl, 3-butynyl, 2-pentynyl or 4-pentynyl, with 2-propynyl being preferred; and when said $C_3$–$C_7$-alkenyl or $C_3$–$C_7$alkynyl are substituted on a heteroatom, then the carbon atoms of said $C_3$–$C_7$alkenyl or $C_3$–$C_7$alkynyl connected to said heteroatom, is saturated; $C_3$–$C_7$cycloalkyl defines cyclopropyl, cyclobutyl, cyclopentyl, cyclohexyl and cycloheptyl, with cyclopentyl and cyclohexyl being preferred; and $C_1$–$C_5$alkanoyl denotes formyl, acetyl, propionyl, butyryl, 2-methylpropionyl, 4-methylbutyryl, 3-methylbutyryl or 2,2-dimethylpropionyl.

As typical examples of mono- and di-(aryl)$C_1$–$C_5$alkyl there may be mentioned phenylmethyl, phenylethyl, 4-chlorophenylmethyl, 4-chlorophenylethyl, 4-methoxyphenylmethyl, 3-methoxyphenylmethyl or diphenylmethyl with phenylmethyl being preferred.

As typical examples of halo substituted $C_1$–$C_5$alkyl and halo substituted $C_1$–$C_5$alkyloxy there may be mentioned fluoromethyl, trifluoromethy, difluoromethyl, chloromethyl, difluoromethoxy and the like.

$C_1$–$C_5$alkanediyl denotes saturated bivalent straight or branch chained hydrocarbon radicals having from 1 to 5 carbon atoms, e.g., methylene, 1,2-ethanediyl, 1,3-propanediyl, 1,4-butanediyl and 1,5-pentanediyl.

$C_5$–$C_7$cycloalkanediyl is generic to, for example, 1,2-cyclopentanediyl, 1,3-cyclopentanediyl, 1,2-cyclohexanediyl, 1,4-cyclohexanediyl and 1,2-cycloheptanediyl.

$C_1$–$C_5$alkanoyl defines formyl, acetyl, propionyl, butyryl, isobutyryl, valeryl, isovaleryl or pivaloyl.

The polycyclic system of formula X attached to the imidazole ring encompasses the following basic structures, which may be unsubstituted os substituted with the substituents $R^3$, $R^4$, $R^5$, $R^6$, $R^7$ and $R^8$ as defined hereinabove:

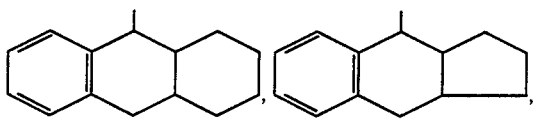
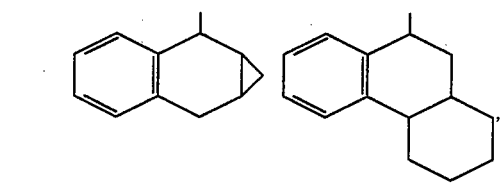
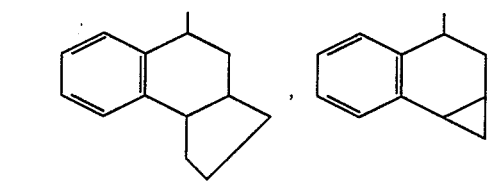
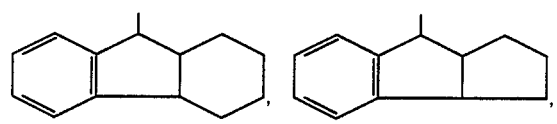
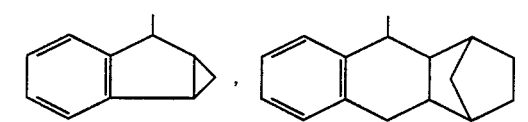
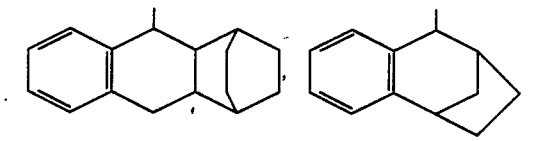
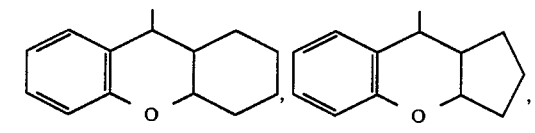
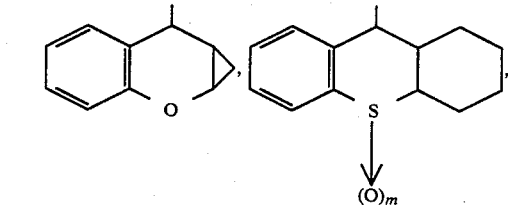

-continued

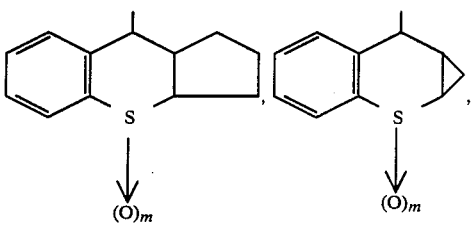
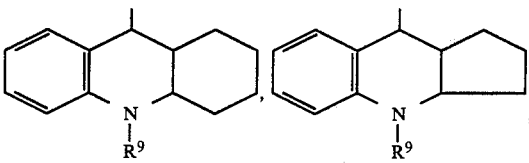
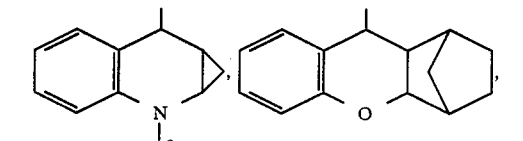
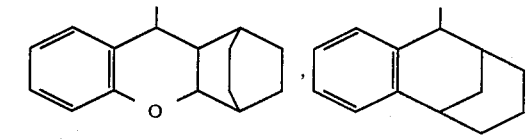

The compounds of formula (I) contain at least one asymmetrical carbon atom, namely the carbon atom of the group X bearing the imidazole moiety, and therefore may exist under different stereochemically isomeric forms. Unless otherwise mentioned or indicated, the chemical designation of compounds denotes the mixtures of all stereochemically isomeric forms. These mixtures contain all diastereomeres and enantiomeres of the basic molecular structure and are intended to be embraced within the scope of the invention.

The absolute configuration of each chiral center may be indicated by the stereochemical descriptors R and S, this R and S notation corresponding to the rules described in Pure Appl. Chem. 1976, 45, 11–30. The relative configuration of the asymmetric centres in the compounds of formula (I) is denoted by cis and trans and where appropriate by the terms α and β, these stereochemical descriptors being used according to the rules described in Chemical Abstracts 1977 Index Guide, Appendix IV, § 203. In some compounds the stereochemical configuration is not experimentally determined. In those cases it is conventionally agreed to designate the stereochemically isomeric form which is first isolated as "A" and the second as "B", without further reference to the actual stereochemical configuration.

Pure stereochemically isomeric forms of the compounds of formula (I) may be obtained by the application of art-known separation methods such as selective crystallization and chromatographic techniques, e.g., counter current distribution, column chromatography, high performance liquid chromatography and the like. Preferably, if a specific stereochemical form is desired, said compound will be synthesized by stereoselective methods of preparation. These methods will advantageously employ enantiomerically pure starting materials.

The invention also comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosporic acid. Preferred salt-forming sulfonic acids are 4-methylbenzenesulfonic acid, benzenesulfonic acid, methanesulfonic acid or trifluoromethanesulfonic acid. Preferred salt-forming carboxylic acids are acetic acid, trifluoracetic acid, benzoic acid, chloroacetic acid, phthalic acid, maleic acid, malonic acid and citric acid. Phosphorus containing acids are the various phosponous acids, phosponic acids and phospinic acids.

Preferred salt-forming alkali metal hydroxids and earth alkaline metal hydroxides are the hydroxids of lithium, sodium, potassium, magnesium or calcium, most preferably those of sodium or potassium. Examples of suitable salt-forming amines are primary, secondary and tertiary aliphatic and aromatic amines such as methanamine, ethanamine, 1-propanamine, 2-propanamine, the four butanamine isomers, N-methylmethanamine, N-ethylethanamine, 2-[(2-hydroxyethyl)amino]ethanol, N-propyl-1-propanamine, N-(1-methylethyl)-2-propanamine, N-butyl-1-butanamine, pyrrolidine, piperidine, morpholine, N,N-dimethylmethanamine, N,N-diethylethanamine, N,N-dipropyl-1-propanamine, quinuclidine, pyridine, quinoline and isoquinoline. Preferred amines are ethanamine, 1-propanamine, N-ethylethanamine or N,N-diethylethanamine, with 2-propanamine, 2-[(2-hydroxyethyl)amino]ethanol and 1,4-diazabicyclo[2.2.2]octane being most preferred. Examples of quaternary ammonium salts generally contain cations arising from ammonium hydroxides or ammonium halide salts, e.g. the tetramethylammonium, the trimethylphenylmethylammonium cation, the triethylphenylmethylammonium, and also the ammonium cation.

Preferred compounds within the present invention are those compounds of formula (I) wherein $R^2$ is hydrogen or $C_1$–$C_7$alkyl; Y is O, S or $CH_2$; A is a $C_1$–$C_5$alkanediyl group being substituted with $R^5$ and $R^6$; and $R^7$ and $R^8$ are each independently hydrogen, halo, $C_1$–$C_5$alkyl, $C_1$–$C_5$alkyloxy, cyano or $C_1$–$C_6$alkylcarbonylamino.

Particularly preferred compounds are those preferred compounds wherein Y is O or $CH_2$; A is $C_{3-5}$ alkanediyl; $R^3$, $R^4$, $R^5$ and $R^6$ are each independently hydrogen or $C_{1-5}$alkyl.

More particularly preferred compounds are those particularly preferred compounds wherein $R^2$ is hydrogen, methyl or ethyl; n is 1 or 2; A is a $C_3$–$C_4$alkanediyl group; $R^3$, $R^4$, $R^5$ and $R^6$ are each independently hydrogen or methyl; and $R^7$ and $R^8$ are each independently hydrogen, methyl, methoxy or halo.

The most preferred compounds within the scope of the present invention are selected from methyl 1-(1,2,3,4,4a,9a-hexahydro-9H-fluoren-9-yl)-1H-imidazole-5-carboxylate and methyl 1-(5,6,7,8-tetrahydro-5,8-methano-9H-benzocyclohept-9-yl)-1H-imidazole-5-carboxylate, the salts or stereochemically isomeric forms thereof.

The preparation of the compounds of formula (I) is generally carried out by the following methods.

The compounds of formula (I) can be obtained by condensing a compound of formula

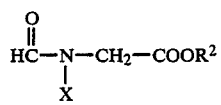

(II)

wherein $R^2$ and X are as defined hereinabove, with a $C_1$–$C_4$alkyl ester of formic acid in the presence of suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

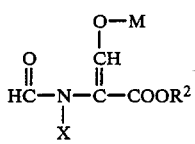

(III)

wherein $R^2$ and X are as defined hereinabove and M is an alkali metal atom, (a) with an alkali metal isothiocyanate in the presence of an acid, thus obtaining a 2-mercaptoimidazole of formula

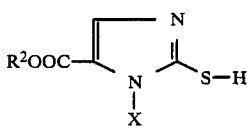

(I-a)

wherein $R^2$ and X are as defined hereinabove, which optionally is converted into a compound of the formula

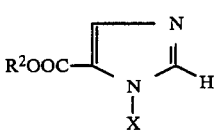

(I-b)

by reacting the starting compound with nitric acid optionally in the presence of an alkali metal initrite, e.g. sodium nitrite; or with Raney-nickel in the presence of a lower aliphatic alcohol, preferably ethanol, at a temperature between 40° C. and 80° C.; or also by treating the starting compounds (I-a) with an aqueous hydrogen peroxide solution preferably in the presence of a carboxylic acid, e.g. acitic acid; or (b) with a carboxylic acid amide of 1 to 3 carbon atoms, preferably formamide, in the presence of an acid at a temperature between 50° C. and 250° C., preferably between 120° C. and 170° C.; or (c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example, 1,1'-oxybisethane, tetrahydrofuran or dioxane; or other aprotic organic solvents. For the cyclization-reaction of the imidazole ring structure, strong mineral acids such as hydrohalic acids, e.g. hydrochloric acid, are most conveniently employed. In the ring-forming variant c) also other acids, e.g. acetic acid, an be used. In this reaction an excess of acid of 5 to 50, preferably of 15 to 40 times the required molar amount is most preferably used. The excess of ammonium salt in this process is 2 to 50, preferably 10 to 30 times the required molar amount.

The compounds of formula (I-b) can also be prepared by the deamination reaction of a 4-amino-1H-imidazole derivative of formula (IV), wherein $R^2$ and X are as defined under formula (I). Said deamination reaction involves a diazotation and a reductive dediazotation step which may be conducted sequentially, i.e. with isolation of the intermediate diazonium salt (IV-a) or in a one-pot fashion wherein said diazonium salt is reduced in situ.

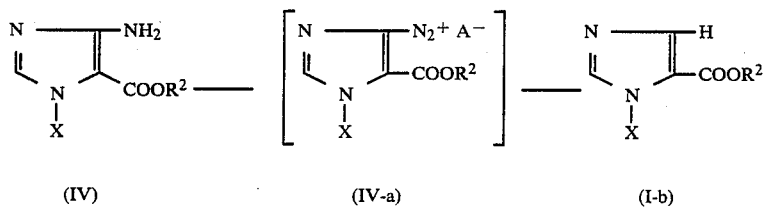

(IV)   (IV-a)   (I-b)

Treatment of the 4-amino-1H-imidazole derivative of formula (IV) in aqueous medium with an alkali metal nitrite, e.g. sodium or potassium nitrite, in the presence of an acid such as hydrochloric acid, sulfuric acid or nitric acid, or with nitronium tetrafluoroborate ($NO^+BF_4^-$) yields the diazonium salt (IV-a). In the latter, $R^2$ and X are as defined under formula (I) and $A^-$ represents an anion corresponding to the conjugated base of the acid employed in the diazotation reaction or the tetrafluoroborate anion. The intermediate diazonium salts (IV-a) are reduced to the compounds of formula (I-b) by treatment with an appropriate reductant such as hypophosphoric acid at an elevated temperature, preferably at the boiling temperature of the reaction mixture.

Alternatively, treatment of the 4-amino-1H-imidazole derivatives of formula (IV) with a $C_1-C_5$alkyl nitrite such as, 1,1-dimethylethyl nitrite or 1,2-dimethylpropyl nitrite in suitable aprotic solvent such as tetrahydrofuran, 1,4-dioxane, trichloromethane or N,N-dimethylformamide yields a compound of formula (I-b) directly. The latter deamination reaction may conveniently be conducted at an elevated temperature, generally at the boiling point of the reaction mixture.

The compound of formula (I) can also be converted into each other following art-known functional group transformation reactions.

The substituent $R^2$ on the carboxylic acid group may be transformed to other substituents encompassed by the definition of $R^2$ by suitable reactions known in the art for the modification of carboxylic acid functions, e.g. by hydrolysis and esterification and/or transesterification.

Y being —S— may be converted to the corresponding sulfoxide or sulfone by an approprioate oxidation procedure, e.g. by treatment with a peroxide or a periodate.

Some of the starting materials for the preparation of the compounds of formula (I) are known, while others are new and can be obtained by known synthesis procedures.

For example, the compounds of formula (II) can be obtained by N-formylating a glycine ester of formula $$X-NH-CH_2-COOR^2 \quad (V)$$

wherein $R^2$ and X are as defined hereinabove, with formic acid in the presence of acetic anhydride. In turn, the compounds of formula (V) can be prepared by N-alkylation an amine of formula $$X-NH_2 \quad (VI)$$

wherein X is defined under formula (I), with an α-haloacetic acid ester, e.g. α-bromoacetic ester, of formula $$Br-CH_2-COOR^2 \quad (VII)$$

wherein $R^2$ is as defined under formula (I). The reaction of (VI) with (VII) is conveniently conducted in a reaction-inert solvent, e.g. tetrahydrofuran, 1,1'-oxybisethane, N,N-dimethylformamide or dichloromethane, in the presence of a base such as an alkali metal carbonate, e.g. sodium carbonate.

The 4-amino-1H-imidazole derivatives of formula (VI) can be obtained by cyclizing an intermediate of formula

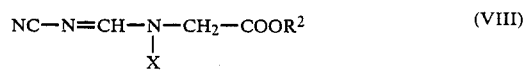

wherein X and $R^2$ are as defined hereinabove under catalysis of a base at elevated temperature in a suitable solvent, e.g. an alcohol. A preferred mode of carrying out said cyclization may comprise the reaction of the starting compound (VIII) in an alcohol, preferably that alcohol of which the ester group $COOR^2$ is derived, in the presence of a catalytic amount of alkoxide obtained by dissolving an alkali metal in said alcohol, at the boiling point of the reaction mixture. Or, alternatively, by reacting (VIII) with an alkali metal alkoxide wherein the alkoxide preferably is $OR^2$ in a polar solvent such as N,N-dimethylformamide or dimethyl sulfoxide. Generally, the reaction temperatures are in the range of +60° C. to +140° C.

The intermediates of formula (VIII) in turn can be prepared by alkylating an amidine of formula $$NC-B=CH-NH-X \quad (IX)$$

wherein X is as defined under formula (I) with an α-haloacetic acid ester of formula (VII), in the presence of an appropriate base, such as, for example an alkali metal hydroxide, an alkali or earth alkaline metal carbonate or hydrogen carbonate, an earth alkaline oxide, an alkali metal alkoxide or trialkylamine, e.g. sodium hydroxide, potassium hydroxide, sodium carbonate, potassium hydrogen carbonate, magnesium oxide, calcium oxide, sodium methoxide, sodium ethoxide, potassium ethoxide, potassium isopropoxide, pyridine, N,N-diethylethanamine and the like. In some instances, the addition of a crown-ether may be recommandable. The reaction may conveniently be conducted at temperatures between +10° C. and the boiling point of the reaction mixture, either without a solvent or in a solvent such as N,N-dimethylformamide, N,N-dimethylacetamide or dimethyl sulfoxide.

The compounds of formula (IX) can be prepared by reacting an amine of formula (VI) with a $C_{1-5}$alkyl-N-cyanomethanimidate of formula

$$C_{1-5}alkyl—O—CH=N—CN \qquad (X)$$

in an appropriate reaction-inert solvent such as trichloromethane, tetrahydrofuran, 1,4-dioxane, acetonitrile, N,N-dimethylformamide or N,N-dimethylacetamide. The said reaction can conveniently be carried out at temperatures between room temperature and the boiling point of the reaction mixture, in particular between +20° C. and +80° C. Removal of the $C_{1-5}$alkanol which is liberated during the course of the reaction and of the solvent by destillation under reduced pressure yields the N-cyanoamidine of formula (IX) which in general need not be purified before further convertion.

The 4-amino-1H-imidazole derivatives of formula (IV) can alternatively be obtained from the amines of formula (VI), by a combined N-alkylating and cyclization reaction in a one-pot procedure. The latter procedure is conducted in the same solvents and bases as mentioned hereinabove for the two step synthesis.

The amines of formula (VI) can be obtained by the reduction of an oxime of formula

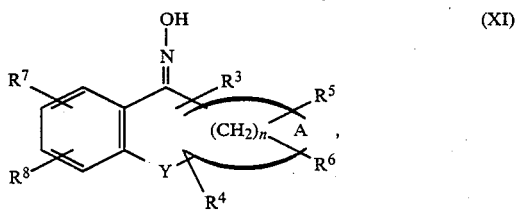

wherein $R^3$, $R^4$, $R^5$, $R^6$, $R^7$, $R^8$, Y, A and n are as defined hereinabove. Said reduction is conveniently conducted with hydrogen in the presence of a noble metal catalyst or with a hydride reagent, e.g. lithium tetrahydroaluminate or diborane in a suitable reaction-inert solvent such as an ether, e.g. tetrahydrofuran, 1,1'-oxybisethane and the like. The oxime of formula (XI) may also be reduced electrochemically.

Said hydroxylamine (XI) in turn, is prepared from the corresponding ketone of formula

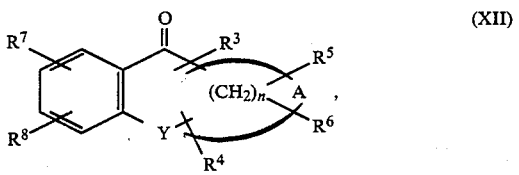

wherein $R^3$, $R^4$, $R^5$, $R^6$, $R^7$, $R^8$, Y, A and n are as defined hereinabove, by reacting said ketone of formula (XII) with hydroxylamine.

The intermediates of formula (V) can also be prepared by the reductive N-alkylation of a ketone of formula (XII) with a glycine ester (XIII) wherein $R^2$ is as defined under formula (I).

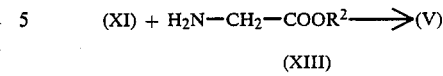
$$(XI) + H_2N—CH_2—COOR^2 \longrightarrow (V)$$
$$(XIII)$$

Said reductive N-alkylation reaction may conveniently be carried out by hydrogenating a stirred and, if desired, heated mixture of the reactants in a suitable reaction-inert organic solvent according to art-known catalytic hydrogenating procedures. Suitable solvents are, for example, alkanols, e.g. methanol, ethanol; ethers, such as tetrahydrofuran. The term "art-known catalytic hydrogenating procedures" means that the reaction is carried out under hydrogen atmosphere and in the presence of a catalyst such as, palladium-on-charcoal and the like. In order to prevent the undesired further hydrogenation of certain functional groups in the reactants and the reaction products it may be advantageous to add an appropriate catalyst-poison to the reaction mixture, e.g. thiophene.

Alternatively, said reductive N-alkylation reactions may be conducted by treating a stirred and, if desired, heated mixture of the reactants with sodium cyanoborohydride, sodium borohydride, formic acid or a salt thereof, e.g. ammonium formiate.

Typical preparation methods of the ketones of formula (XI) are described in e.g. J. Org. Chem. 1967, 32, 3358, J. Org. Chem. 1970, 35 1183, J. Org. Chem. 1978, 43, 849, J. Org. Chem. 1985, 50, 5132, J. Am. Chem. Soc. 1960, 82, 1457–1462, J. Am. Chem. Soc. 1948, 70, 974, J. Am. Chem. Soc. 1973, 95, 5659.

The compounds of formula (I) are stable compounds and no precautionary measures are required for handling them.

When used at the indicated rates of application, the compounds of formula (I) have good selective herbicidal properties which make them most suitable for use in crops of useful plants, in particular in sugar beet, soybeans, cereals and preferably in maize and rice. In some cases damage is also caused to weeds which up to now have only been controlled with total herbicides.

At higher rates of application, all tested plants are so severely damaged in their development that the die.

The invention also relates to herbicidal compositions containing one or more inert carriers and, if desired, other adjuvants and as an active ingredient a herbicidally effective amount of a compound of formula (I) as defined hereinabove. Further the invention relates to a method of controlling weeds, said method comprising the application to said weeds or to the locus thereof of a herbicidally effective amount of a compound of formula (I), a sterieoisomeric form thereof or a salt.

In the method for controlling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared by known means, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, theylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, epiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfacants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, synthetic surfactants are used, especially fatty sulfonates, fatty sulfates, sulfonated benzimidazole derivatives or alkylarylsulfonates.

The fatty sulfonates or sulfates usually occur as alkali metal salts, earth alkaline metal salts or unsubstitued or substituted ammonium salts and contain an alkyl radical consisting of 8 to 22 carbon atoms, said alkyl also comprising radicals derived from acyl groups of fatty acids, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminipolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least on $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich and Vienna, 1981, M. and J. Ash, "Encyclopedia of Surfactants", Vol. I–III, Chemical Publishing Co., N.Y., 1980–81.

The herbicidal compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
| --- | --- |
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 88 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |

-continued

Granulates
active ingredient:  0.5 to 30%, preferably 3 to 15%
solid carrier:      99.5 to 70%, preferably 97 to 85%

The following examples are intended to illustrate and not to limit the scope of the present invention in all its aspects. Unless otherwise stated all parts therein are by weight.

EXPERIMENTAL PART

A. Preparation of Intermediates

Example 1

(a) A mixture of 48 parts of 1,2,3,4,4a,9a-hexahydro-9H-fluoren-9-one, 65 parts of methyl glycine hydrochloride, 65 parts of sodium acetate and 560 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated. The residue was taken up in a mixture of water and trichloromethane. The whole was acidified with a hydrochloric acid solution. The separated aqueous layer was made alkaline and the product was extracted with trichloromethane. The combined organic layers were dried, filtered and evaporated, yielding 16.6 parts (24.8% of methyl N-(1,2,3,4,4a,9a-hexahydro-9H-fluoren-9-yl) glycine as a residue (int. 1).

(b) A mixture of 16.6 parts of methyl N-(1,2,3,4,4a,9a-hexahydro-9H-fluoren-9-yl)glycine, 44 parts of formic acid and 11.9 parts of acetic acid anhydride was stirred overnight at room temperature. The reaction mixture was poured into water and the product was extracted with trichloromethane. The extract was dried, filtered and evaporated, yielding 15.9 parts (86.4%) of methyl N-formyl-N-(1,2,3,4,4a,9a-hexahydro-9H-fluoren-9-yl)glycine as a residue (int. 2).

Example 2

A mixture of 23.4 parts of 2,3,3a,8a-tetrahydrocyclopent[a]inden-8(1H)-one, 31.4 parts of methyl glycine hydrochloride, 1 part of a solution of thiophene in methanol 4%, 400 parts of methanol and 13.3 parts of potassium acetate was hydrogenated at normal pressure and at room temperature with 2.0 parts of palladium-on-charcoal catalyst 10%. After the calculated amount of hydrogen was taken up, the catalyst was filtered off and the filtrate was evaporated. The residue was taken up in water and the product was extracted with dichloromethane. The extract was washed with a hydrochloric acid solution and a sodium hydroxide solution, dried, filtered and evaporated, yielding 29.0 parts (86.9%) of methyl N-(1,2,3,3a,8,8a-hexahydrocyclopent[a]inden-8yl)glycine as a residue (int. 3).

By the same method there were also prepared methyl N-(1,1a,6,6a-tetrahydrocycloprop[a]inden-6yl)glycine as a residue (int 4); and methyl N-(5,6,7,8-tetrahydro-5,8-methano-9H-benzocyclohept-9yl)glycine as a residue (int. 5).

Example 3

A mixture of 46.4 parts of 2,3,4,4a,10,10a-hexahydro-9(1H)phenanthrenone, 58 parts of methyl glycine monohydrochloride, 2 parts of a solution of thiophene in methanol 4%, 480 parts of methanol and 26.1 parts of potassium fluoride was hydrogenated at normal pressure and at 50° C. with 3.0 parts of palladium-on-charcoal catalyst 10%. After the calculated amount of hydrogen was taken up, the catalyst was filtered off and the filtrate was evaporated. The residue was taken up in water and 1,1'-oxybisethane. The whole was treated with a sodium hydroxide solution. The separated organic layer was dried, filtered and evaporated, yielding 59.5 parts (93.8%) of methyl N-(1,2,3,4,4a,9,10,10a-octahydro-9-phenanthrenyl)glycine as a residue (int. 6).

By the same method there was also prepared methyl [4aα,10β,10aβ]-N-(1,2,3,4,4a,9a-hexahydro-9H-xanthen-9-yl)glycine as a residue (int. 7).

The glycine derivatives obtained in examples 2 and 3 were subsequently N-formylated following the procedures described in example 1 b) and yielded respectively methyl N-formyl-N-(1,2,3,3a,8,8a-hexahydrocyclopent[a]inden-8-yl)glycine as a residue (int. 8);

methyl N-formyl-N-(1,1a,6,6a-tetrahydrocycloprop[a]inden-6-yl)glycine as a residue (int. 9);

methyl N-formyl-N-(5,6,7,8-tetrahydro-5,8-methano-9H-benzocyclohept-9-yl)glycine as a residue (int. 10);

methyl N-formyl-N-(1,2,3,4,4a,9,10,10a-octahydro-9-phenanthrenyl)glycine as a residue (int. 11) and methyl ([4ax,10B,10ax]-N-formyl-N-(1,2,3,4,4a,9a-hexahydro-9H-xanthen-9-yl)glycine (int. 12).

EXAMPLE 4

(a) 4.3 Parts of a syn-anti-mixture of 9-oximino-1,2,3,4,4a,9,9a,10-octahydroanthracene were dissolved in 40 ml of tetrahydrofuran and 8.7 ml of methanolic hydrochloric acid. 1.3 Parts of a 10% palladium-on-carbon catalyst were added and the mixture was hydrogenated with 896 ml gaseous hydrogen at 30–35° C. and normal pressure within 30 minutes. The catalyst was filtered off, and the filtrate concentrated. 4 Parts of 9-amino-1,2,3,4,4a,9,9a,10-octahydroanthracene hydrochloride, mp. 240–245° C., were obtained. The hydrochloride was dissolved in water, and sodium hydroxide was added to adjust the pH-value to pH 8. The alkaline solution was extracted with ether. The combined etheral phases were dried with $Na_2SO_4$, filtered and concentrated. 2.8 Parts (70% of theory) of 9-amino-1,2,3,4,4a,9,9a,10-octahydroanthracene (int. 13), mp. 37–39° C., were obtained. The amine-product consists of a mixture of at least 3 stereochemical isomers.

(b) 20 Parts of 9-amino-1,2,3,4,4a,9,9a,10-octahydroanthracene were dissolved in 100 ml of ethanol. 9.8 Parts of ethyl N-cyano-formamidate were added within 10 minutes and the mixture was heated to reflux. The cooled solution was concentrated. 24.9 Parts (99% of theory) of crude N-(1,2,3,4,4a,9,9a,10-octahydroanthracene-9-yl)-N'-cyano-formamidine (int. 14), mp. 145–165° C. were obtained.

(c) 20.8 Parts of N-(1,2,3,4,4a,9,9a,10-octahydroanthracene-9-yl)-N'-cyano-formamidine were dissolved in 140 ml of N,N-dimethylformamide together with 0.1 parts of 18-crown-6. 28.4 Parts of potassium carbonate were added. The mixture was heated to +80° C. and 13.8 Parts of α-bromo-methyl-acetate were added. After 15 hours at +80° C. to +100° C. the reactants were poured on ice and the mixture was extracted with ether. The etheral extracts were dried with $Na_2SO_4$, filtered and concentrated. 21 Parts of crude residue were chromatographed on a silica gel column and extracted with an ethyl acetate/hexane mixture (1:1). 11.6 Parts (43%) of methyl 1-(1,2,3,4,4a,9,9a,10-octahydroanthracene-9-yl)-4amino-1H-imidazole-5-carboxylate (int. 15), mp. 155–159° C. were isolated.

B. Preparation of Final Compounds

Example 5

(a) A mixture of 27.3 parts of methyl N-formyl-N-(1,2,3,3a,8,8a-hexahydrocyclopent[a]inden-8-yl)glycine, 4.8 parts of a sodium hydride dispersion 50%, 30 parts of methyl formate and 225 parts of tetrahydrofuran was stirred overnight at room temperature. After the addition of 8 parts of methanol, the mixture was evaporated. The residue was taken up in water and 1,1′-oxybisethane. The separated aqueous layer was acidified with concentrated hydrochloric acid and the product was extracted with dichloromethane. The extract was dried, filtered and evaporated. A mixture of the residue, 200 parts of methanol, 30 parts of concentrated hydrochloric acid, 19.5 parts of potassium thiocyanate and 250 parts of water was stirred overnight at 60° C. After the addition of 450 parts of water, the product was filtered off and dried in vacuo at 60° C., yielding 15.1 parts (48.0%) of methyl (A)-1-(1,2,3,3a,8,8a-hexahydrocyclopent[a]inden-8-yl)-2-mercapto-1H-imidazole-5-carboxylate; mp. 154.2° C. (compound 4.1).

(b) A mixture of 14.1 parts of methyl (A)-1-(1,2,3,3a,8,8a-hexahydrocyclopent[a]inden-8-yl)-2-mercapto-1H-imidazole-5-carboxylate, 0.1 parts of sodium nitrite, 75 parts of concentrated nitric acid and 150 parts of water was stirred for 1 hour at room temperature. After the addition of crushed ice, the whole was treated with a sodium hydroxide solution. The product was extracted with dichloromethane. The extract was dried, filtered and evaporated. The residue was converted into the nitrate salt in a mixture of 1,1′-oxybisethane and 2-propanone. The salt was filtered off and dried, yielding 11.1 parts (71.4%) of methyl (A)-1-(1,2,3,3a,8,8a-hexahydrocyclopent[a]inden-8-yl)-2-mercapto-1H-imidazole-5-carboxylate mononitrate; mp. 148.1° C. (compound 4.2).

Following the same procedures there were also obtained:

methyl 1-(1,2,3,4,4a,9a-hexahydro-9H-fluoren-9-yl)-1H-imidazole-5-carboxylate mononitrate; mp. 140.2° C. (compound 1.4);

methyl 1-(1,1a,6,6a-tetrahydrocycloprop[a]inden-6-yl)-1H-imidazole-5-carboxylate mononitrate; mp. 169.0° C. (compound 4.9);

methyl 1-(5,6,7,8-tetrahydro-5,8-methano-9H-benzocyclohept-9-yl)-1H-imidazole-5-carboxylate monohydrochloride; mp. 153.6° C. (compound 5.2); and methyl [4aα,10β, 10aα]-1-(1,2,3,4a,9a-hexahydro-9H-xanthen-9-yl)-1H-imidazole-5-carboxylate mononitrate, hemihydrate; mp. 184.6° C. (compound 2.20).

(c) A mixture of 8.8 parts of methyl (A)-1-(1,2,3,3a,8,8a-hexahydrocyclopent[a]inden-8-yl)-1H-imidazole-5-carboxylate mononitrate, 5 parts of a sodium hydroxide solution 50% and 250 parts of water was stirred for 2 hours at reflux temperature. The reaction mixture was acidified with acetic acid. The precipitated product was filtered off and dried, yielding 5.45 parts (79.6%) of (A)-1-(1,2,3,3a,8,8a-hexahydrocyclopent[a]inden-8-yl)-1H-imidazole-5-carboxylic acid; mp. 216.6° C. (compound 4.3).

Example 6 methyl 2-mercapto-1-(1,2,3,4,4a,9,10,10a-octahydro-9-phenanthrenyl)-1H-imidazole-5-carboxylate (compound 3.1) was prepared following the reaction procedure described in example 4a).

A mixture of 19.0 parts of methyl 2-mercapto-1-(1,2,3,4,4a,9,10,10a-octahydro-9-phenanthrenyl)-1H-imidazole-5-carboxylate, 75 parts of nitric acid and 150 parts of water was stirred for 1 hour at room temperature. The reaction mixture was diluted with crushed ice and treated with a sodium hydroxide solution. The product was extracted with 1,1′-oxybisethane. The extract was dried, filtered and evaporated. The residue was crystallized from acetonitrile. The product was filtered off and dried, yielding 1.9 parts (11.1%) of methyl 1-(1,2,3,4,4a,9,10,10a-octahydro-9-phenanthrenyl)-1H-imidazole-5-carboxylate; mp. 139.9° C. (compound 3.2).

The latter compound and compound 5.2 were converted to their respective carboxylic acid following the saponification procedure described in example 4c), yielding 1-(1,2,3,4,4a,9,10,10a-octahydro-9-phenanthrenyl)-1H-imidazole-5-carboxylic acid (compound 3.3); and 1-(5,6,7,8-tetrahydro-5,8-methano-9H-benzocyclohept-9-yl)-b 1H-imidazole-5-carboxylic acid; mp. 230.0° C. (compound 5.3).

Example 7

4.3 Parts of 1,1-dimethylethyl nitrite were dissolved in 40 ml N,N-dimethylformamide and heated to +60° C. A solution of 8 parts of methyl 1-(1,2,3,4,4a,9,9a,10-octahydroanthracen-9-yl)-4-amino-1H-imidazole-5-carboxylate in 50 ml N,N-dimethylformamide was dropwise added at +60° C. After 1.5 hour the solution was poured into water and extracted with ethyl acetate. The organic phase was dried with Na$_2$SO$_4$, filtered and concentrated. The resulting 8.5 parts of crude material were chromatographed on a silica gel column with an ethyl acetate/hexane mixture (1:1). 2.9 Parts (38%) of methyl 1-(1,2,3,4,4a,9a,10-octahydroanthracen-9-yl)-imidazole-5-carboxylate, mp. 151–152° C. (compound 2.2), were obtained. According to $^1$H-NMR the product consists of an epimeric mixture of 2 isomers.

All other compounds listed in tables 1 to 6 can be obtained by analogous methods of preparation.

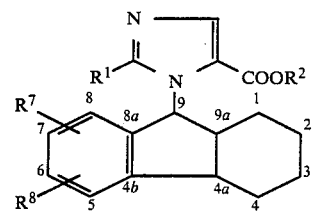

| comp. No. | R$^1$ | R$^2$ | R$^7$ | R$^8$ | physical data |
|---|---|---|---|---|---|
| 1.1 | SH | CH$_3$ | H | H | solid residue |
| 1.2 | H | CH$_3$ | H | H | |
| 1.3 | H | H | H | H | |
| 1.4 | H | CH$_3$ | H | H | .HNO$_3$/mp. 140.2° C. |
| 1.5 | H | CH$_3$ | H | H | cis |
| 1.6 | H | CH$_3$ | H | H | trans |
| 1.7 | SH | C$_2$H$_5$ | H | H | |
| 1.8 | H | C$_2$H$_5$ | H | H | |
| 1.9 | SH | i. C$_3$H$_7$ | H | H | |
| 1.10 | H | i. C$_3$H$_7$ | H | H | |
| 1.11 | SH | n. C$_3$H$_7$ | H | H | |
| 1.12 | H | n. C$_3$H$_7$ | H | H | |
| 1.13 | SH | n. C$_4$H$_9$ | H | H | |
| 1.14 | H | n. C$_4$H$_9$ | H | H | |

-continued

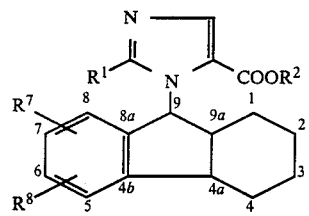

| comp. No. | R¹ | R² | R⁷ | R⁸ | physical data |
|---|---|---|---|---|---|
| 1.15 | SH | —CH₂CH=CH₂ | H | H | |
| 1.16 | H | —CH₂CH=CH₂ | H | H | |
| 1.17 | SH | —CH₂C≡CH | H | H | |
| 1.18 | H | —CH₂C≡CH | H | H | |
| 1.19 | SH | cyclohexyl | H | H | |
| 1.20 | H | cyclohexyl | H | H | |
| 1.21 | SH | —CH₂OCH₃ | H | H | |
| 1.22 | H | —CH₂OCH₃ | H | H | |
| 1.23 | SH | —CH₂C₆H₅ | H | H | |
| 1.24 | H | —CH₂C₆H₅ | H | H | |
| 1.25 | SH | CH₃ | 6-F | H | |
| 1.26 | H | CH₃ | 6-F | H | |
| 1.27 | H | H | 6-F | H | |
| 1.28 | SH | CH₃ | 6-Cl | H | |
| 1.29 | H | CH₃ | 6-Cl | H | |
| 1.30 | SH | CH₃ | 6-Br | H | |
| 1.31 | H | CH₃ | 6-Br | H | |
| 1.32 | SH | CH₃ | 6-CH₃O | H | |
| 1.33 | H | CH₃ | 6-CH₃O | H | |
| 1.34 | SH | CH₃ | 6-CH₃ | H | |
| 1.35 | H | CH₃ | 6-CH₃ | H | |
| 1.36 | SH | CH₃ | 6-Cl | 8-Cl | |
| 1.37 | H | CH₃ | 6-Cl | 8-Cl | |
| 1.38 | SH | CH₃ | 6-CH₃ | 8-CH₃ | |
| 1.39 | H | CH₃ | 6-CH₃ | 8-CH₃ | |

TABLE 1a

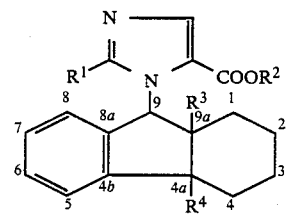

| Comp. No. | R¹ | R² | R³ | R⁴ | physical data |
|---|---|---|---|---|---|
| 1.40 | SH | CH₃ | CH₃ | H | |
| 1.41 | H | CH₃ | CH₃ | H | |
| 1.42 | SH | CH₃ | CH₃ | CH₃ | |
| 1.43 | H | CH₃ | CH₃ | CH₃ | |

TABLE 2

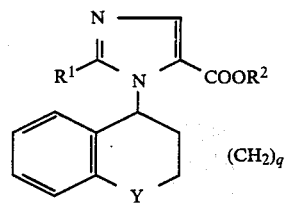

| comp. No. | R¹ | R² | Y | q | physical data |
|---|---|---|---|---|---|
| 2.1 | SH | CH₃ | CH₂ | 4 | |
| 2.2 | H | CH₃ | CH₂ | 4 | mp. 151–152° C. |
| 2.3 | H | H | CH₂ | 4 | |
| 2.4 | SH | CH₃ | CH₂ | 3 | |
| 2.5 | H | CH₃ | CH₂ | 3 | |
| 2.6 | H | H | CH₂ | 3 | |
| 2.7 | SH | CH₃ | CH₂ | 3 | trans |

TABLE 2-continued

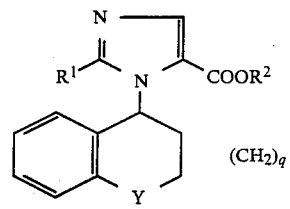

| comp. No. | R¹ | R² | Y | q | physical data |
|---|---|---|---|---|---|
| 2.8 | SH | CH₃ | CH₂ | 3 | cis |
| 2.9 | H | CH₃ | CH₂ | 3 | trans |
| 2.10 | H | CH₃ | CH₂ | 3 | cis |
| 2.11 | H | H | CH₂ | 3 | trans |
| 2.12 | H | H | CH₂ | 3 | cis |
| 2.13 | SH | CH₃ | CH₂ | 2 | |
| 2.14 | H | CH₃ | CH₂ | 2 | |
| 2.15 | H | H | CH₂ | 2 | |
| 2.16 | SH | CH₃ | CH₂ | 1 | |
| 2.17 | H | CH₃ | CH₂ | 1 | |
| 2.18 | H | H | CH₂ | 1 | |
| 2.19 | SH | CH₃ | O | 4 | (4aα, 10β, 10aα) |
| 2.20 | H | CH₃ | O | 4 | .HNO₃.1/2H₂O/mp. 184.6° C. (4aα, 10β, 10aα) |
| 2.21 | H | H | O | 4 | |
| 2.22 | SH | CH₃ | O | 3 | |
| 2.23 | H | CH₃ | O | 3 | |
| 2.24 | H | H | O | 3 | |
| 2.25 | SH | CH₃ | S | 4 | |
| 2.26 | H | CH₃ | S | 4 | |
| 2.27 | H | H | S | 4 | |
| 2.28 | SH | CH₃ | SO | 4 | |
| 2.29 | H | CH₃ | SO | 4 | |
| 2.24 | SH | CH₃ | SO₂ | 4 | |
| 2.25 | H | CH₃ | SO₂ | 4 | |
| 2.26 | SH | CH₃ | N—C(O)—CH₃ | 4 | |
| 2.27 | H | CH₃ | N—C(O)—CH₃ | 4 | |
| 2.28 | SH | CH₃ | N—CH₃ | 4 | |
| 2.29 | H | CH₃ | N—CH₃ | 4 | |

TABLE 3

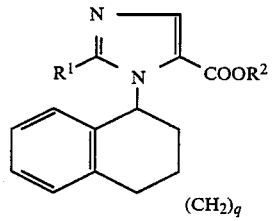

| comp. No. | R¹ | R² | q | physical data |
|---|---|---|---|---|
| 3.1 | SH | CH₃ | 4 | |
| 3.2 | H | CH₃ | 4 | mp. 139.9° C. |
| 3.3 | H | H | 4 | |
| 3.4 | SH | CH₃ | 3 | |
| 3.5 | H | CH₃ | 3 | |
| 3.6 | H | H | 3 | |
| 3.7 | SH | CH₃ | 1 | |
| 3.8 | H | CH₃ | 1 | |

TABLE 4

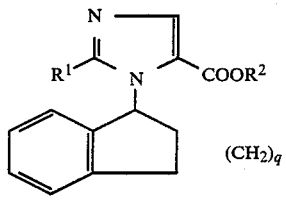

| comp. No. | R¹ | R² | q | physical data |
|---|---|---|---|---|
| 4.1 | SH | $CH_3$ | 3 | A; mp. 154.2° C. |
| 4.2 | H | $CH_3$ | 3 | A; .$HNO_3$/mp. 148.1° C. |
| 4.3 | H | H | 3 | A; mp. 216.6° C. |
| 4.4 | SH | $C_2H_5$ | 3 | |
| 4.5 | H | $C_2H_5$ | 3 | |
| 4.6 | SH | i-$C_3H_7$ | 3 | |
| 4.7 | H | i-$C_3H_7$ | 3 | |
| 4.8 | SH | $CH_3$ | 1 | solid residue |
| 4.9 | H | $CH_3$ | 1 | $HNO_3$/mp. 169.0° C. |
| 4.10 | H | $C_2H_5$ | 3 | |
| 4.11 | H | $CH_2-CH=CH_2$ | 1 | |
| 4.12 | H | $CH_2-CH=CH_2$ | 1 | |

TABLE 5

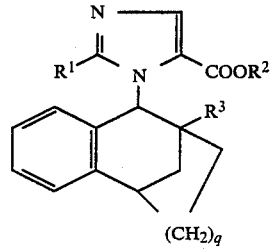

| Comp. No. | R¹ | R² | R³ | q | Physical data |
|---|---|---|---|---|---|
| 5.1 | SH | $CH_3$ | H | 1 | solid residue |
| 5.2 | H | $CH_3$ | H | 1 | HCl/mp. 153.6° C. |
| 5.3 | H | H | H | 1 | mp. 230.0° C. |
| 5.4 | H | $C_2H_5$ | H | 1 | |
| 5.5 | SH | $CH_3$ | H | 2 | |
| 5.6 | H | $CH_3$ | H | 2 | |
| 5.7 | H | H | H | 2 | |
| 5.8 | SH | $CH_3$ | $CH_3$ | 1 | |
| 5.9 | H | $CH_3$ | $CH_3$ | 1 | |
| 5.10 | H | H | $CH_3$ | 1 | |
| 5.11 | SH | $CH_3$ | $C_2H_5$ | 1 | |
| 5.12 | H | $CH_3$ | $C_2H_5$ | 1 | |
| 5.13 | H | H | $C_2H_5$ | 1 | |

TABLE 6

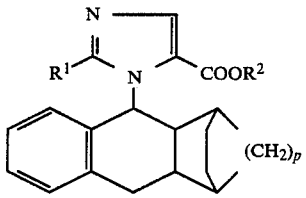

| comp. No. | R¹ | R² | p | physical data |
|---|---|---|---|---|
| 6.1 | SH | $CH_3$ | 1 | |
| 6.2 | H | $CH_3$ | 1 | |
| 6.3 | H | H | 1 | |
| 6.4 | SH | $CH_3$ | 2 | |
| 6.5 | H | $CH_3$ | 2 | |
| 6.6 | H | H | 2 | | c. Composition examples

Example 8:

Composition exampled for solid compounds of formula (I) (percentages are by weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4–5 moles of ethylene oxide) | 3% | 3% |
| clacium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | |
|---|---|
| compound of formula (I) | 3% |
| polyethylene glycol (mol. wt. 200) | 2% |
| kaolin | 95% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | |
|---|---|
| compound of formula (I) | 5% |
| isopropylamine | 1% |
| octylphenol polyethylene glycol ether (78 moles of ethylene oxide) | 3% |
| water | 91% |

Example 9:

Composition examples for liquid active ingredients of formula (i) (throughout, percentages are by weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N-methyl-2-pyrrolidone | — | 20% | — | — |
| epoxidised coconut oil | — | — | 1% | 5% |
| petroleum distillate (boiling range 160-190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carariers with the active ingredient.

D. Biological examples

Example 10:

Preemergence herbicidal activity

In the greenhouse, seeds of test plants are sown in plastic pots, filled with a sandy soil which subsequently are covered by a 0.5 cm layer of the same soil. The test compounds are dissolve din aceton (100 mg compound in 4 ml aceton), and further diluted with tap water immediately before application. Each pot receives 20 ml test solution, which is evenly distributed over the soil surface by means of a plastic syringe. The dilution of the test solution is made in such a way that the amount of active ingredient, per pot, is 4 pl kg per hectare in the first test, and 2 kg per hectare in the second test. Test plants are mentioned in the table 1.

During the whole test period (4 weeks) the pots are kept on benches under normal greenhouse conditions. Temperature and humidity fluctuate according to the time of the day and to the season. The herbicidal activity is evaluated by scoring the above-ground growth of the plant following a semi-logarithmic scale:

1: no effect (growth comparable to the untreated plants).
2: 2.5% effect
3: 5% effect
4: 10% effect
5: 15% effect
6: 25% effect
7: 35% effect
7-8: 50% effect
8: 67.5% effect
9: 100% effect (complete killing of the plants)

note: a score 8.9 indicates that the herbicidal activity was about 85%, whereas a score (8) 9 indicates that said activity was closer to 9 than to 8 and 8 (9) closer to 8 than to 9.

| | rates in kg/ha | | | | | | | | |
|---|---|---|---|---|---|---|---|---|---|
| | Compound 1.4 | | Compound 4.2 | | Compound 4.5 | | Compound 5.2 | | Compound 5.3 | |
| | 4 | 2 | 4 | 2 | 4 | 2 | 4 | 2 | 4 | 2 |
| Lolium | 8.9 | 6 | 9 | 6 | 8.9 | 6 | 9 | (8)9 | 3 | 1 |
| Echinochloa | 9 | 9 | 9 | 6 | 7 | 8 | 9 | 9 | 9 | 8.9 |
| Setaria | (8)9 | 8 | (8)9 | 8.9 | 9 | 8 | 9 | 9 | 9 | 8 |
| Bromus | 8 | 6 | 8 | 9 | 6 | 3 | 9 | 8.9 | 8 | 1 |
| Poa | 9 | (8)9 | 9 | 9 | 9 | 8 | 9 | 9 | 9 | 8 |

-continued

| | rates in kg/ha | | | | | | | | |
|---|---|---|---|---|---|---|---|---|---|
| | Compound 1.4 | | Compound 4.2 | | Compound 4.5 | | Compound 5.2 | | Compound 5.3 |
| | 4 | 2 | 4 | 2 | 4 | 2 | 4 | 2 | 4 | 2 |
| Digitaria | 9 | 9 | 9 | 9 | 9 | 7 | 9 | 9 | 8.9 | 7 |
| *Avena fatua* | (7)8 | 6 | (7)8 | 3 | 6 | 6 | 9 | 7.8 | 9 | 1 |

Example 11:

Herbicidal action against paddy rice associated weeds

Paddy rice was sown in plastic containers (60 cm² surface, 500 ml by volume) together with either the seeds of the waterweeds Echinochloa crus galli or Monochoria vaginalis. The containers were watered up to the soil surface and after three days the water level was raised slightly above the soil surface (3–5 mm). Three days after sowing an aqueous emulsion of the active compound was applied by spraying the containers at a rate of application of 4 kg of a.i. per hectare (dilution 550 1/ha). The containers were kept in a greenhouse for three weeks under conditions optimal for the waterweeds, i.e. at a temperature between 20° and 25° C. and under high humidity. The evaluation of the tests was made in accordance with the rating given in example 10.

Results

Dosage: 4 kg a.i. per hectare

| Comp. No. | Echinochloa | Monochoria |
|---|---|---|
| 1.4 | 9 | 9 |
| 2.2 | 9 | 9 |
| 4.1 | 9 | 9 |
| 4.2 | 9 | 9 |
| 4.3 | 9 | 9 |

We claim:
1. A compound of the formula:

$$R^1 \text{ structure with } COOR^2 \quad (I)$$

a stereochemically isomeric form thereof, or a salt thereof, wherein:
$R^1$ represents hydrogen or mercapto;
$R^2$ represents hydrogen, $C_{1-7}$alkyl, $C_{3-7}$alkenyl, $C_{3-7}$alkynl, Cphd 3-7cycloalkyl, $C_{1-7}$alkyloxy-$C_{1-7}$alkyl, or aryl$C_{1-5}$alkyl; and
X represents a group of the formula:

(structure with $R^3$, $R^4$, $R^5$, $R^6$, $R^7$, $R^8$, $(CH_2)_n$, A, Y)

wherein:
Y represents O or S(O) wherein m represents zero, one, or two;
n represents 1, 2, or 3;
A represents $C_{1-5}$alkanediyl or $C_{5-7}$cycloalkanediyl;
$R^3$, $R^4$, $R^5$, and $R^6$ each independently represent hydrogen, $C_{1-5}$alkyl, mono- and di(aryl)$C_{1-5}$alkyl, $C_{1-5}$alkloxy, halo, $C_{3-7}$alkenyl, $C_{1-5}$alkyl substituted with one to three halo atoms, $C_{1-5}$alkyloxy substituted with one to three halo atoms, or aryl;
wherein the groups $R^3$, $R^4$, and the bivalent group A as defined above may be substituted on any carbon atom making up the Y-containing part of the tricyclic ring system, including any of the $CH_2$ moieties of the $-(CH_2)_n-$ and Y fragments; provided that the bivalent group A is not connected to the same carbon atom thus forming a spirocyclic ring system; and
$R^7$ and $R^8$ each independently represent hydrogen, $C_{1-5}$alkyl, $C_{1-5}$alkyloxy, halo, $C_{1-5}$alkyl substituted with one to three halo atoms, $C_{1-5}$alkyloxy substituted with one to three halo atoms, cyano, nitro, amino, mono- and di($C_{1-5}$alkyl)amino, or $C_{1-5}$alkyl-carbonylamino; and
wherein aryl represents phenyl optionally substituted with up to three substituents each independently selected from $C_{1-5}$alkyl, $C_{1-5}$alkyloxy, and halo.

2. A compound according to claim 1 wherein $R^2$ is hydrogen or $C_1-C_7$alkyl; Y is O, S; A is a $C_1-C_5$alkanediyl group being substituted with $R^5$ *pl and R6*; and $R^7$ and $R^8$ are each independently hydrogen, halo, $C_1-C_5$alkyl, $C_1-C_5$alkyloxy, cyano or $C_1-C_6$alkylcarbonylamino.

3. A compound according to claim 2 wherein Y is O; A is $C_{3-5}$alkanediyl; $R^3$, $R^4$, $R^5$ and $R^6$ are each independently hydrogen or $C_{1-5}$alkyl.

4. A compound according to claim 3 wherein $R^2$ is hydrogen, metnyl or ethyl; n is 1 or 2; A is a $C_3-C_4$alkanediyl group; $R^3$, $R^4$, $R^5$ and $R^6$ are each independently hydrogen or methyl; and $R^7$ and $R^8$ are each independently hydrogen, methyl, methoxy or halo.

5. A herbicidal composition comprising an inert carrier and, if desired, other adjuvants, and as active ingredient a herbicidally effective amount of a chemical compound having the formula (I) as claimed in claim 1.

6. A herbicidal composition according to claim 5 wherein $R^2$ is hydrogen or $C_1-C_7$alkyl; Y is O or S; A is a $C_1-C_5$alkane-diyl group being substituted with $R^5$ and $R^6$; and $R^7$ and $R^8$ are each independently hydrogen, halo, $C_1-C_5$alkyl, $C_1-C_5$alkyloxy, cyano or $C_1-C_6$alkyl-carabonylamino.

7. A herbiacidal composition according to claim 6 wherein Y is O; A is $C_{3-5}$alkanediyl; $R^3$, $R^4$, $R^5$ and $R^6$ are each independently hydrogen or $C_{1-5}$alkyl.

8. A herbicidal composition according to claim 7 wherein $R^2$ is hydrogen, methyl or ethyl; n is 1 or 2; A is a $C_3-C_4$alkanediyl group; $R^3$, $R^4$, $R^5$ and $R^6$ are each independently hydrogen or methyl; and $R^7$ and $R^8$ are each independently hydrogen, methyl, methoxy or halo.

9. A method for controlling weeds, which method comprises applying to said weeds or to the locus thereof of a herbiacidally effective amount of a chemical compound having the formula (I) as claimed in claim 1.

10. A method according to claim 9 for selectively controlling weeds in crops of useful plants.

11. A method according to claim 10 wherein the crop is rice, maize or cereals.

12. A method according to claim 10 wherein the crop is rice and the rice is transplanted rice.

13. A method according to claim 11 wherein 0.01 to 5.0 kg of active ingredient per hectare are applied to areas where rice crops are grown.

14. A method according to claim 13 wherein 0.05 to 1 kg of the active ingredient is applied per hectare after transplanting the rice plantlets.

15. A method according to claim 9 wherein $R^2$ pl is hydrogen or $C_1$-$C_7$alkyl: Y is O or S; A is a $C_1$-$C_5$alkanediyl group being substituted with $R^5$ and $R^6$; and $R^7$ and $R^8$ are each independently hydrogen, halo, $C_1$-$C_5$alkyl, $C_1$-$C_5$alkyloxzy, cyano or $C_1$-$C_6$alkylcarbonylamino.

16. A method according to claim 15 wherein Y is O; A is $C_{3\text{-}14}$ 5alkanediyl; $R^3$, $R^4$, $R^5$ and $R^6$ are each independently hydrogen or $C_{1\text{-}5}$alkyl.

17. A method according to claim 16 wherein $R^2$ is hydrogen, methyl or ethyl; n is 1 or 2; A is a $C_3$-$C_4$alkanediyl group; $R^3$, $R^4$, $R^5$ and $R^6$ are each independently hydrogen or methyl; and $R^7$ and $R^8$ are each independently hydrogen, methyl, methoxy or halo.

* * * * *